United States Patent
Fusejima et al.

(10) Patent No.: US 7,678,843 B2
(45) Date of Patent: Mar. 16, 2010

(54) DENTAL RESTORATIVE MATERIAL COMPOSITION

(75) Inventors: Futoshi Fusejima, Itabashi-ku (JP); Naoko Jimbo, Itabashi-ku (JP); Shinji Kaga, Itabashi-ku (JP)

(73) Assignee: GC Corporation, Tokyo (JP)

( * ) Notice: Subject to any disclaimer, the term of this patent is extended or adjusted under 35 U.S.C. 154(b) by 131 days.

(21) Appl. No.: 11/858,403

(22) Filed: Sep. 20, 2007

(65) Prior Publication Data

US 2008/0081849 A1    Apr. 3, 2008

(30) Foreign Application Priority Data

Sep. 28, 2006 (JP) ............................. 2006-265998

(51) Int. Cl.
| | |
|---|---|
| C08J 3/28 | (2006.01) |
| C08F 2/50 | (2006.01) |
| A61K 6/04 | (2006.01) |
| A61K 6/083 | (2006.01) |

(52) U.S. Cl. ...................... 523/117; 523/109; 523/113; 523/115; 523/116; 522/90; 522/70; 522/74; 522/71; 522/81; 522/83; 522/96; 522/150; 522/173; 522/174; 522/178; 522/181; 524/436

(58) Field of Classification Search ................ 523/116, 523/115, 117, 109, 113; 524/436; 522/90, 522/70, 74, 71, 83, 81, 96, 150, 152, 153, 522/173, 174, 178, 181
See application file for complete search history.

(56) References Cited

U.S. PATENT DOCUMENTS

| | | | | |
|---|---|---|---|---|
| 4,388,069 A | * | 6/1983 | Orlowski | 523/116 |
| 4,649,165 A | * | 3/1987 | Kuhlmann | 523/116 |
| 5,356,951 A | * | 10/1994 | Yearn et al. | 523/116 |

* cited by examiner

*Primary Examiner*—Sanza L McClendon
(74) *Attorney, Agent, or Firm*—Oblon, Spivak, McClelland, Maier & Neustadt, L.L.P.

(57) ABSTRACT

To provide a dental restorative material composition using an organic-inorganic composite filler having excellent surface smoothness like a natural tooth, low polymerization shrinkage, excellent X-ray contrast imaging property, similar transparency to that of a natural tooth, and no variation of transparency before and after the composition is hardened, the dental restorative material composition includes (a) a (meth)acrylate monomer, (b) an organic-inorganic composite filler having an average particle diameter of 5 to 50 μm which is made by mixing a (meth)acrylate monomer and a fine particle filler having an average primary particle diameter of 0.005 to 0.3 μm and having X-ray impermeability, (c) a fine particle filler having an average primary particle diameter of 0.005 to 0.04 μm, and (d) a photopolymerization initiator.

14 Claims, No Drawings

DENTAL RESTORATIVE MATERIAL COMPOSITION

BACKGROUND OF THE INVENTION

1. Field of the Invention

The present invention relates to a dental restorative material composition which is properly used for filling and restoring a cavity of a dental caries.

2. Description of the Conventional Art

A dental restorative material composition, e.g., a dental composite resin, has been required to have X-ray contrast imaging property in order to confirm it after a dental treatment. A dental restorative material composition generally includes a monomer to be a base material at the time of a polymerization, a filler such as a glass powder, and a polymerizing catalyst to harden the monomer. A glass powder as a filler has a maximum particle diameter of 1 to 2 μm. In the conventional dental restorative material composition, a dental restorative material after hardening obtains X-ray contrast imaging property by blending a material having X-ray contrast imaging property in the glass powder.

However, a glass powder having a maximum particle diameter of 1 to 2μm has a problem that a dental restorative material composition becomes easily sticky, that is, when the composition is filled in a tooth by using an exclusive spatula, the composition is adhered to the spatula so that operativity decreases. Since this glass powder has a large specific surface area of a particle, it is necessary to include a large amount of monomer component in a dental restorative material composition. Thus, the ratio of the glass powder occupying in a dental restorative material composition decreases. As a result of this, there is a problem that a dental restorative material after hardening is largely shrunk by polymerization.

In order to improve the above-described sticky problem and large polymerization shrinkage problem, for example, Japanese Unexamined Patent Publication No. 5-194135 discloses a dental restorative material composition using an organic-inorganic composite filler having an average particle diameter of 5 to 50 μm made by mixing a monomer and a glass powder having a particle diameter of 1 to 2μm, polymerizing and hardening the mixture, and pulverizing it. However, it is hard to obtain high X-ray contrast imaging property by only the glass powder. Further, when a glass powder is used, a composition is influenced by refractive index of the glass powder, and thus it is necessary to adjust a refractive index of a glass powder with a refractive index of a product after polymerization. However, since the refractive index of a monomer is varied by polymerizing and hardening the monomer, a relationship between the refractive indexes of a glass powder and a monomer is varied after and before hardening those, and thus transparency is damaged.

When a particle diameter of a filler is smaller, a dental restorative material composition is more hardly influenced by a refractive index of the filler. Thus, for example, Japanese Patent Publication No. 3-10603 and Unexamined Japanese Patent Publication No. 10-130116 disclose a composite resin using an organic-inorganic composite filler made by mixing a monomer and a fine particle filler having an average primary particle diameter of 0.005 to 0.04 μm, polymerizing and hardening the mixture, and pulverizing it. However, organic-inorganic composite fillers using a fine particle filler in these prior arts use colloidal silica not having X-ray contrast imaging property as the fine particle filler. Thus, there is a problem that there is almost no X-ray contrast imaging property required for a dental restorative material composition.

On the other hand, in order to give X-ray contrast imaging property to the composition, for example, Japanese Translation of PCT Publication No. 2003-512407 discloses a dental restorative material composition made by directly blending a material, e.g., a metal oxide or a metal fluoride, with a composition as a filler. However, when the metal oxide or metal fluoride has an average particle diameter of 0.5 to 1 μm, a refractive index of the metal oxide or the metal fluoride is not adjusted with the refractive index of a monomer after hardening, and thus there is a problem that a hardened dental restorative material composition cannot has similar transparency to that of a natural tooth. Even in the case of using a material, e.g., a metal oxide or a metal fluoride, having an average particle diameter of less than 0.5 μm, if the material is not blended in an organic-inorganic composite filler but is directly mixed in the composition, there is a still problem that operativity of the composition is inferior like the case of the conventional fine particle filler.

SUMMARY OF THE INVENTION

A primary objective of the present invention is to provide a dental restorative material composition using an organic-inorganic composite filler having excellent surface smoothness like a natural tooth and low polymerization shrinkage, in which the dental restorative material composition has excellent X-ray contrast imaging property and similar transparency to that of a natural tooth, and further the transparency is not varied before and after the composition is hardened.

Present inventors found out, to complete the present invention, that the above-described problems can be solved by making a dental restorative material composition with a combination of a monomer, an organic-inorganic composite filler made by mixing and hardening a monomer and a fine particle filler having X-ray contrast imaging property and pulverizing the mixture, a fine particle filler having a specific diameter, and a photopolymerization initiator.

That is, the present invention is a dental restorative material composition including:

(a) a (meth)acrylate monomer;

(b) an organic-inorganic composite filler having an average particle diameter of 5 to 50 μm, which is made by mixing a (meth)acrylate monomer and a fine particle filler having an average primary particle diameter of 0.005 to 0.3 μm and having X-ray impermeability and hardening and pulverizing the mixture;

(c) a fine particle filler having an average primary particle diameter of 0.005 to 0.04 μm; and (d) a photopolymerization initiator.

Further, the dental restorative material composition according to the present invention preferably includes (e) a glass powder having a maximum particle diameter of 0.5 to 4 μm or less and an average particle diameter of 0.03 to 3 μm.

A dental restorative material composition according to the present invention uses an organic-inorganic composite filler capable of lowering a polymerization shrinkage and suppressing stickiness of a paste. Since a fine particle filler in the organic-inorganic composite filler has X-ray contrast imaging property, the composition can have clinically sufficient X-ray contrast imaging property. Further, since the fine particle filler included in the organic-inorganic composite filler is small, the dental restorative material composition can have high transparency without blocking visible beam. Furthermore, since the fine particle filler is small, an influence from the refractive index of the filler is low, and thus variation of transparency after and before polymerization is not influenced. So, the dental restorative material composition is excellent.

DETAILED DESCRIPTION OF PREFERRED EMBODIMENT

A (meth)acrylate monomer as a component (a) used in a dental restorative material composition according to the present invention is a methacrylate or acrylate monomer. More particularly, the monomer is methyl(meth)acrylate, ethyl(meth)acrylate, isopropyl(meth)acrylate, n-butyl (meth) acrylate, isobutyl(meth)acrylate, hydroxypropyl(meth)acrylate, tetrahydrofurfuryl(meth)acrylate, glycidyl(meth) acrylate, 2-hydroxyethyl(meth)acrylate, 2-hydroxypropyl (meth)acrylate, 3-hydroxypropyl(meth)acrylate, 2-methoxyethyl(meth)acrylate, 2-ethoxyethyl(meth)acrylate, 2-methoxyethyl(meth)acrylate, 2-ethylhexyl(meth) acrylate, benzyl(meth)acrylate, 2-hydroxy-1,3-di(meth) acryloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth) acrylate, trimethylolpropane tri(meth)acrylate, trimethylolethane tri(meth)acrylate, pentaerythritol tri(meth)acrylate, trimethylolmethane tri(meth)acrylate, pentaerythritol tetra (meth)acrylate, polybutylene glycol di(meth)acrylate, or bisphenol A diglycidyl (meth)acrylate. A (meth)acrylate having a urethane bond is di-2-(meth)acryloxyethyl-2,2,4-trimethylhexamethylene dicarbamate, or 1,3,5-tris[1,3-bis{(meth)acryloyloxy}-2-propoxycarbonylaminohexane]-1,3, 5-(1H, 3H, 5H) triazine-2,4,6-trione. Further, a (meth) acrylate having a urethane bond is (meth)acrylate of a urethane oligomer including 2,2'-di(4-hydroxycyclohexyl) propane, 2-oxypanone, hexamethylene diisocyanate, and 2-hydroxyethyl (meth)acrylate, or (meth)acrylate of a urethane oligomer including 1,3-butanediol, hexamethylene diisocyanate, and 2-hydroxyethyl(meth)acrylate.

These methacrylate or acrylate monomers is publicly known as a dental material, and thus these can be used independently or by mixing if necessary. The ratio of the monomer is 5 to 50% by weight with respect to the whole dental restorative material composition.

An organic-inorganic composite filler of the component (b) is made by mixing a (meth)acrylate monomer and a fine particle filler having an average primary particle diameter of 0.005 to 0.3 µm and having X-ray impermeability, hardening the mixture, and pulverizing it. A raw material of the fine particle filler having X-ray impermeability is an alkali earth metal compound having an atomic number of higher than 20, e.g., strontium fluoride, strontium carbonate, barium oxide, or barium carbonate, a transition element having an atomic number of higher than 39 or its compound, e.g., zirconia, yttrium oxide, yttrium fluoride, or zirconia oxide, or a lanthanoid compound, e.g., lanthanum fluoride, lanthanum oxide, ytterbium fluoride, or ytterbium oxide. These materials can be used by combining two or more among those. The ratio of the component (b) is 35 to 80% by weight.

When an organic-inorganic composite filler, which is made by mixing a (meth)acrylate monomer and a fine particle filler having an average primary particle diameter of 0.005 to 0.3 µm and having X-ray impermeability, hardening the mixture, and pulverizing it, is used in a dental restorative material composition, the composition can have X-ray contrast imaging property in clinical, excellent surface smoothness, and a low polymerization shrinkage. Further, since the fine particle filler has a small particle diameter and does not block visible beam, the composition can keep transparency. The transparency is not varied before and after polymerization. Furthermore, since the average primary particle diameter of the fine particle filler included in the organic-inorganic composite filler is small to be 0.005 to 0.3 µm, polishing property of the composite is not influenced even when a particle diameter of the organic-inorganic composite filler is large.

The monomer and the fine particle filler having an average primary particle diameter of 0.05 to 0.3 µm and having X-ray impermeability are mixed by a mixer, hardened, and pulverized. Then, in order to increase dispersibility at the time of mixing the monomer and the fine particle filler having X-ray impermeability, it is preferable to mix a fine particle filler having an average primary particle diameter of 0.005 to 0.04 µm, e.g., colloidal silica, which is the component (c) as mentioned below, with the monomer and the fine particle filler. As a hardening agent to harden an organic-inorganic composite filler, an organic peroxide or an azo compound can be used by dissolving in the case of thermal hardening. Further, a photopolymerization initiator can be used in the case of photohardening. In addition, a chemical polymerization at ordinary temperature can be used.

An average particle diameter of the organic-inorganic composite filler is 5 to 50 µm. When the diameter is less than 5 µm, the effect to improve the polymerization shrinkage problem or the stickiness problem is low. When the diameter is more than 50 µm, the surface smoothness is inferior. A blending amount of the organic-inorganic composite filler to the dental restorative material composition is preferably 35 to 80% by weight. When the amount is less than 35% by weight, the effect to improve the polymerization shrinkage problem or the stickiness problem is low. When the amount is more than 80% by weight, the operativity of the composition may be inferior.

The fine particle filler (c) having an average primary particle diameter of 0.005 to 0.04 µm is colloidal silica which is generally used, and the filler is blended within the whole amount of a dental restorative material composition to prevent separation of the monomer component. The blending amount of the filler (c) is preferably 1 to 8% by weight with respect to the whole dental restorative material composition.

A photopolymerization initiator of the component (d) is generally used by combining a sensitizer and a reducing agent. The sensitizer is camphorquinone, benzyl, diacetyl, benzyl dimethyl ketal, benzyl diethyl ketal, benzyl di(2-methoxyethyl)ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropyl thioxanthone, 2-chloro-7-trifluoromethylthioxanthone, thioxanthone-10,10-dioxide, thioxanthone-10-oxide, benzoinmethyl ether, benzomethyl ether, isopropyl ether, benzoinisobutyl ether, benzophenon, bis(4-dimethylaminophenyl)ketone, 4,4'-bisdiethylaminobenzophenon, or a compound including an azido group. These can be used independently or by mixing.

As the reducing agent, a tertiary amine is generally used. The tertiary amine is preferably dimethylaminoethyl methacrylate, triethanol amine, methyl 4-dimethylaminobenzoate, ethyl 4-dimethylaminobenzoate, or isoamyl 4-dimethylaminobenzoate. Another reducing agent is benzoyl peroxide, an organic metal compound, or a sulfinic acid derivative. A photopolymerizable dental restorative material composition obtained by the above-described method can be polymerized and reacted by irradiating active beam such an ultraviolet radiation or a visible radiation to it.

A beam source is various kinds of an ultra-high voltage, high-voltage, medium-voltage or low voltage mercury lamp, a chemical lamp, a carbon arc lamp, a metal halide lamp, a fluorescence lamp, a tungsten lamp, a xenon lamp, or an argon ion laser. In addition, small amounts of an ultraviolet absorber, a colorant, and a polymerization inhibitor can be used if necessary.

In a dental restorative material composition according to the present invention, a glass powder having a maximum particle diameter of 0.5 to 4 μm or less and an average particle diameter of 0.03 to 3 μm is added as a component (e) in an amount of 10 to 50% by weight, in order to increase the strength of a composite resin. A composition of the glass powder is not especially limited if it is a composition to form a glass. As the glass having X-ray contrast imaging property, a glass containing an alkali earth metal atom such as calcium, strontium or barium, a zinc glass, and a lead glass can be used. Of course, the glass is not limited to the glass having X-ray contrast imaging property, but a glass without having X-ray contrast imaging property, such as a quartz glass, can be used. Further, the glass having X-ray contrast imaging property can be used by combining the glass without having X-ray contrast imaging property.

EXAMPLE

Examples are described below more particularly. The following methacrylate monomers or acrylate monomers are used in Examples and Comparative examples.
UDMA: di-2-(meth)acryloxyethyl-2,2,4-trimethyl-hexamethylene dicarbamate
3G: triethyleneglycol dimethacrylate
Bis-GMA:
2,2-bis[4-(2-hydroxy-3-methacryloxypropoxy)phenyl]propane,
1,3-BG: 1,3-butanediol dimethacrylate,
Bis-MPEPP: 2,2-bis(4-methacryloxypolyethoxyphenyl) propane,
TMPT: triethyleneglycol trimethacrylate The following organic-inorganic composite fillers are made using ytterbium fluoride or a zirconia powder as a fine particle filler having an average primary particle diameter of 0.005 to 0.3 μm and having X-ray contrast imaging property.

<Organic-Inorganic Composite Filler A>
An organic-inorganic composite filler A is made by mixing 50% by weight of ytterbium fluoride (having an average primary particle diameter of 0.04 μm) and 50% by weight of a mixed liquid including UDMA and 3G at the weight ratio of 5:5 and 1% by weight of azoisobutyronitrile, thermally hardening the mixture, and pulverizing it so as to have an average particle diameter of 10 μm.

<Organic-Inorganic Composite Filler B>
An organic-inorganic composite filler B is made by mixing 30% by weight of a zirconia powder (having an average primary particle diameter of 0.003 μm) and 70% by weight of a mixed liquid including UDMA and 3G at the weight ratio of 5:5 and 1% by weight of azoisobutyronitrile, thermally hardening the mixture, and pulverizing it so as to have an average particle diameter of 10 μm.

<Organic-Inorganic Composite Filler C>
An organic-inorganic composite filler C is made by mixing 40% by weight of a mixed liquid including 1% by weight of azoisobutyronitrile in TMPT, 50% by weight of ytterbium fluoride (having an average primary particle diameter of 0.04 μm), and 10% by weight of colloidal silica (the product name: Aerosil R-972, produced by Nippon Aerosil Corporation) as a fine particle filler, thermally hardening the mixture, and pulverizing it so as to have an average particle diameter of 15 μm.

<Organic-Inorganic Composite Filler D>
An organic-inorganic composite filler D is produced by mixing 50% by weight of ytterbium fluoride (having an average primary particle diameter of 0.05 μm) and 50% by weight of a mixed liquid including UDMA and Bis-MPEPP at the weight ratio of 5:5 and 1% by weight of azoisobutyronitrile, thermally hardening the mixture, and pulverizing it so as to have an average particle diameter of 8 μm.

<Organic-Inorganic Composite Filler E>
An organic-inorganic composite filler E is produced by mixing 50% by weight of ytterbium fluoride (having an average primary particle diameter of 0.1 μm) and 50% by weight of a mixed liquid including UDMA and 3G at the weight ratio of 5:5 and 1% by weight of azoisobutyronitrile, thermally hardening the mixture, and pulverizing it so as to have an average particle diameter of 10 μm.

Glass Powder

<Glass Powder A>
Quarts glass (having an average particle diameter of 1 μm)

<Glass Powder B>
Aluminosilicate glass including strontium (having an average particle diameter of 1 μm)

EXAMPLE 1

A paste is made by mixing 25% by weight of Bis-MPEPP (a photopolymerization initiator is made by dissolving 0.5 weight parts of camphorquinone as a photosensitizer and 1 weight parts of dimethylaminoethyl methacrylate as a reducing agent with respect to 100 weight parts of the whole monomer liquid), 70% by weight of the organic-inorganic composite filler D, and 5% by weight of colloidal silica (the product name: Aerosil R-972, produced by Nippon Aerosil Corporation) as a fine particle filler of component (c). Mixing is carried out using a mixer in a darkroom. Then, the following tests were carried out to the obtained restorative material.

(1) Bending Strength Test
The restorative material is pressed into a mold having dimensions of 2 mm×2 mm×25 mm by a glass plate through a cellophane paper, and irradiated for 60 seconds by a visible beam irradiator (the product name: G-Light, produced by GC Corporation) from the upper direction of one side of the restorative material so as to hit the beam to the whole. The obtained sample is dipped in water for 24 hours, and subjected to a three-point bending test by an auto graph (produced by Shimadzu Seisakusyo Corporation) at a span of 20 mm and a crosshead speed of 1 mm/min.

(2) X-ray contrast imaging property
A Test of X-Ray Contrast Imaging Property is carried out according to ISO4049-2000.

(3) Filling State
1. A cavity is formed to an evulsion tooth of a cow tooth by giving a round bevel having a depth of 2 mm and a diameter of 3 mm.

2. A restorative material is filled and hardened in the cavity using a dental bond (the product name: UNIFIL BOND, produced by GC Corporation).
3. After the sample is hardened, the sample is dipped in water at 37° C. for 24 hours, and is subjected to a thermal cycle test of 2000 times at 4° C. to 60° C. for 30 seconds in a basic fuchsin aqueous solution.
4. After the thermal cycle test, a center part of the cavity is horizontally cut along a plane vertical with respect to a tooth axis, the cross section is polished to be smooth in pouring water by an emery paper No. 1000.
5. The filling state is determined by an invasion degree of fuchsin between the restorative material and the tooth. The determination is carried out by an evaluation of 4 stages of a to d, that is, a: the filling state is excellent and there is no invasion, b: there is slight invasion into enamels, c: there is invasion into a dentin, and d: there is invasion into a cavity bottom part.

(4) Ten Point Average Roughness

The restorative material is pressed into a mold having an inner diameter of 20 mm and a thickness of 2 mm by a glass plate through a cellophane paper and irradiated for 60 seconds by a visible beam irradiator (the product name: G-Light, produced by GC Corporation) from the upper direction of one side of the restorative material so as to hit the beam to the whole. Just after finishing the irradiation, an irradiated surface of the sample is polished by an emery paper No. 600 and an emery paper No. 1000, and then is finally polished using an abrasive (the product name: DIA SHINE, produced by GC Corporation). Then, a ten point average roughness of a finally polished surface is measured using a surface roughness tester (produced by Kosaka Laboratory Corporation).

(5) Transparency

The restorative material is pressed into a mold having an inner diameter of 15 mm and a thickness of 1.5 mm by a glass plate through a cellophane paper and irradiated for 60 seconds by a visible beam irradiator (the product name: G-Light, produced by GC Corporation) from the upper direction of one side of the restorative material so as to hit the beam to the whole. A value of L* of the hardened sample is measured on a white surface and a black surface of a concealment rate measuring paper (JIS K 5400) by a tester (the product name: Spectrophotometer CM-3610d, produced by KONICA MINOLTA Corporation). The difference ΔL in lightness between the value of L* on the white surface and that on the black surface is calculated so that transparency was obtained.

(6) Variation of Transparency

The restorative material is pressed into a mold having an inner diameter of 15 mm and a thickness of 1.5 mm by a glass plate through a cellophane paper. Then, the glass plate is removed, and a value of L* before hardening the material is measured on the black surface of a concealment rate measuring paper (JIS K 5400) by a tester (the product name: Spectrophotometer CM-3610d, produced by KONICA MINOLTA Corporation). Then, the material is irradiated for 60 seconds by a visible beam irradiator (the product name: G-Light, produced by GC Corporation) from the upper direction of one side of the restorative material so as to hit the beam to the whole. The value of L* of the hardened material is measured on the black surface of a concealment rate measuring paper (JIS K 5400) by a tester (the product name: Spectrophotometer CM-3610d, produced by KONICA MINOLTA Corporation). The difference ΔL in lightness between the value of L* before hardening the material and that after hardening the material is calculated so that the variation of transparency was obtained.

Blending compositions and blending amounts of dental restorative material compositions used in Examples and Comparative examples and results of respective tests are collectively shown in Table 1.

EXAMPLES 2 to 8

Dental restorative materials are made using similar blending compositions and blending amounts in Table 1 of Example 1 and subjected to similar tests to those of Example 1. These results are also shown in Table 1. (A photopolymerizable initiator in a monomer is similar to that of Example 1, and Comparative examples use the same photopolymerizable initiator)

TABLE 1

| | (a) + (d) (Meth)acrylate Monomer (% by weight) | | (b) Organic-inorganic Composite Filler (% by weight) | | (c) Fine Particle Filler (% by weight) | | (e) Glass Powder (% by weight) | | Bending Strength (MPa) | X-ray Contrast Imaging Property (with respect to Al %) | Filling State | Point Average Roughness (um) | Transparency (ΔL) | Variation of Transparency (ΔL) |
|---|---|---|---|---|---|---|---|---|---|---|---|---|---|---|
| Example 1 | Bis-MPEPP | 25 | D | 70 | Colloidal Silica | 5 | | | 102 | 265 | a | 0.48 | 25.8 | 11.2 |
| Example 2 | UDMA | 30 | A | 67 | Colloidal Silica | 3 | | | 110 | 248 | a | 0.52 | 24.2 | 10.7 |
| Example 3 | UDMA 3G | 15 15 | C | 67 | Colloidal Silica | 3 | | | 95 | 245 | a | 0.55 | 20.5 | 12.8 |
| Example 4 | Bis-GMA Bis-MPEPP 1.3RG | 10 5 10 | D | 72 | Colloidal Silica | 3 | | | 113 | 271 | a | 0.51 | 22.7 | 13.2 |
| Example 5 | Bis-GMA 3G | 15 10 | D | 70 | Colloidal Silica | 5 | | | 100 | 266 | a | 0.49 | 21.6 | 11.6 |
| Example 6 | UDMA 3G | 20 5 | B | 72 | Colloidal Silica | 3 | | | 97 | 157 | a | 0.52 | 20.4 | 10.3 |
| Example 7 | UDMA 3G | 15 15 | C | 37 | Colloidal Silica | 3 | A | 30 | 115 | 218 | a | 0.68 | 16.1 | 6.4 |
| Example 8 | UDMA 3G | 15 15 | C | 27 | Colloidal Silica | 3 | A B | 30 10 | 124 | 203 | a | 0.74 | 17.2 | 5.9 |
| Example 9 | UDMA 3G | 15 15 | E | 67 | Colloidal Silica | 3 | | | 92 | 244 | a | 0.54 | 18.3 | 14.6 |

COMPARATIVE EXAMPLE 1

As an organic composite filler, which has been conventionally used and does not have X-ray contrast imaging property, a dental restorative material composition including an organic-inorganic composite filler F is produced by mixing 70% by weight of a mixed liquid which includes UDMA and 3G at the weight ratio of 5:5, and 1% by weight of azoisobutyronitrile, and 30% by weight of colloidal silica (the product name: Aerosil R-972, produced by Nippon Aerosil Corporation) as a fine particle filler, thermally hardening the mixture, and pulverizing it so as to have an average particle diameter of 16 μm.

A paste is made by mixing 25% by weight of Bis-MPEPP (a photopolymerization initiator is made by dissolving 0.5 weight parts of camphorquinone as a photosensitizer and 1 weight part of dimethylaminoethyl methacrylate as a reducing agent with respect to 100 weight parts of the whole monomer liquid), 70% by weight of the organic-inorganic composite filler F as an organic-inorganic composite filler, and 5% by weight of colloidal silica (the product name: Aerosil R-972, produced by Nippon Aerosil Corporation) as a fine particle filler. Mixing is carried out using a mixer in a darkroom. The paste is subjected to similar tests to those of Examples with compositions and blending amounts shown in Table 2, and these results are collectively shown in Table 2. The filling state, the ten point average roughness, the transparency, and the variation of transparency are sufficient, but the paste does not have X-ray contrast imaging property.

COMPARATIVE EXAMPLE 2

A restorative material including a quartz glass powder, which is generally called as a conventional type, is subjected to the tests. A quartz glass powder having a maximum particle diameter of 50 μm and an average particle diameter of 20 μm is used as a glass powder C, and the restorative material including the glass powder C is subjected to similar tests to those of Examples with compositions and blending amounts shown in Table 2. The X-ray contrast imaging property, the filling state, and the ten point average roughness are insufficient.

COMPARATIVE EXAMPLE 3

An amino silicate glass (having an average particle diameter of 1 μm) including the organic-inorganic composite filler F used in Comparative example 1 and strontium is used as glass powder B. A restorative material including the glass powder B is subjected to similar tests to those of Examples with compositions and blending amounts shown in Table 2. The X-ray contrast imaging property is insufficient.

COMPARATIVE EXAMPLE 4

An organic-inorganic composite filler G is made by mixing 50% by weight of a mixed liquid which includes UDMA and 3G at the weight ratio of 5:5 and 1% by weight of azoisobutyronitrile, and 50% by weight of a glass powder having an average particle diameter of 20 μm as an inorganic filler, thermally hardening the mixture, and pulverizing it so as to have an average particle diameter of 16 μm. A dental restorative material composition is made with compositions and blending amounts shown in Table 2, and subjected to similar tests to those of Examples. The X-ray contrast imaging property, the filling state, and the ten point average roughness are insufficient.

COMPARATIVE EXAMPLE 5

A dental restorative material composition is made with compositions and blending amounts shown in Table 2 using a barium glass having an average particle diameter of 1 μm as a glass powder D, and subjected to similar tests to those of Examples. The filling state, the transparency, and the variation of transparency are insufficient.

COMPARATIVE EXAMPLE 6

An organic-inorganic composite filler H is produced by mixing 50% by weight of a mixed liquid which includes UDMA and 3G at the weight ratio of 5:5 and 1% by weight of azoisobutyronitrile, and 50% by weight of ytterbium fluoride having an average primary particle diameter of 1 μm as an inorganic filler, thermally hardening the mixture, and pulverizing it so as to have an average particle diameter of 16 μm. A dental restorative material composition is made with compositions and blending amounts shown in Table 2, and subjected to similar tests to those of Examples. The X-ray contrast imaging property and the filling state are sufficient. However, the ten point average roughness is somewhat rough, and the transparency and the variation of transparency are insufficient.

COMPARATIVE EXAMPLE 7

A dental restorative material composition is made by blending a fine particle filler having an average primary particle diameter of 0.005 to 0.3 μm or less and having X-ray contrast imaging property, and ytterbium fluoride (having an average primary particle diameter of 0.05 μm). These materials are not prepared to be an organic-inorganic composite filler, but blended to the dental restorative material composition as it is as a fine particle filler. The dental restorative material composition is made with compositions and blending amounts shown in Table 2, and subjected to similar tests to those of Examples. The X-ray contrast imaging property, the transparency, and the variation of transparency are sufficient, but the filling state is insufficient.

TABLE 2

| | (a) + (d) (Meth)acrylate Monomer (% by weight) | | (b) Organic-inorganic Composite Filler (% by weight) | | (c) Fine Particle Filler (% by weight) | | (e) Glass Powder (% by weight) | | Results of Tests | | | | | |
|---|---|---|---|---|---|---|---|---|---|---|---|---|---|---|
| | | | | | | | | | Bending Strength (MPa) | X-ray Contrast Imaging Property (with respect to Al %) | Filling State | Point Average Roughness (um) | Transparency (ΔL) | Variation of Transparency (ΔL) |
| Comparative example 1 | Bis-MPEPP | 25 | A | 70 | Colloidal Silica | 5 | | | 102 | 20 | a | 0.48 | 25.8 | 11.2 |
| Comparative example 2 | UDMA | 30 | | | Colloidal Silica | 3 | A | 67 | 148 | 20 | b | 3.42 | 14.2 | 13.8 |
| Comparative example 3 | UDMA 3G | 15 15 | A | 30 | Colloidal Silica | 3 | B | 37 | 98 | 120 | a | 0.64 | 16.8 | 6.2 |
| Comparative example 4 | UDMA 3G | 20 5 | B | 22 | Colloidal Silica | 3 | B | 50 | 121 | 140 | b | 4.25 | 15.8 | 5.8 |
| Comparative example 5 | Bis-GMA 3G | 15 10 | | | Colloidal Silica | 5 | C | 70 | 162 | 198 | c | 0.64 | 7.5 | 20.2 |
| Comparative example 6 | UDMA 3G | 20 5 | C | 70 | Colloidal Silica | 5 | | | 105 | 260 | a | 2.18 | 8.6 | 22.6 |
| Comparative example 7 | Bis-MPEPP | 50 | | | Colloidal Silica Ytterbium Fluoride | 10 40 | | | 84 | 325 | d | 0.52 | 21.2 | 11.7 |

What is claimed is:

1. A dental restorative material composition comprising:
   (a) a (meth)acrylate monomer;
   (b) an organic-inorganic composite filler having an average particle diameter of 5 to 50 μm, which is made by mixing a (meth)acrylate monomer and a fine particle filler having an average primary particle diameter of 0.005 to 0.3 μm and having X-ray impermeability, wherein a raw material of the fine particle filler having X-ray impermeability is at least one material selected from the group consisting of a transition element having an atomic number of higher than 39 or its compound, and a lanthanoid compound;
   (c) a fine particle filler having an average primary particle diameter of 0.005 to 0.04 μm; and
   (d) a photopolymerization initiator.

2. The dental restorative material composition as claimed in claim 1, further comprising:
   (e) a glass powder having a maximum particle diameter of 0.5 to 4 μm or less and an average particle diameter of 0.03 to 3 μm.

3. The dental restorative material composition as claimed in claim 1, wherein the transition element or its compound is at least one selected from the group consisting of zirconia, yttrium oxide, yttrium fluoride, and zirconia oxide.

4. The dental restorative material composition as claimed in claim 1, wherein the lanthanoid compound is at least one selected from the group consisting of lanthanum fluoride, lanthanum oxide, ytterbium fluoride, and ytterbium oxide.

5. The dental restorative material composition as claimed in claim 1, wherein a amount of the fine particle filler in (b) is 50 wt. % or less based in the total amount of the organic-inorganic composite filler.

6. The dental restorative material composition as claimed in claim 1, wherein a amount of the (meth)acrylate monomer (a) is from 5 to 50 wt. % based on the total amount of the dental restorative material composition.

7. The dental restorative material composition as claimed in claim 1, wherein a amount of the organic-inorganic composite filler is from 35 to 80 wt. % based on the total amount of the dental restorative material composition.

8. The dental restorative material composition as claimed in claim 1, wherein a amount of the fine particle filler (c) is from 1 to 8 wt. % based on the total amount of the dental restorative material composition.

9. The dental restorative material composition as claimed in claim 2, wherein a amount of the glass powder (e) is from 10 to 50 wt. % based on the total amount of the dental restorative material composition.

10. The dental restorative material composition as claimed in claim 1, further comprising a hardening agent.

11. The dental restorative material composition as claimed in claim 1, wherein the photopolymerization initiator (d) comprises a combination of a sensitizer and a reducing agent.

12. The dental restorative material composition as claimed in claim 11, wherein the sensitizer is at least one compound selected from the group consisting of camphorquinone, benzyl, diacetyl, benzyl dimethyl ketal, benzyl diethyl ketal, benzyl di(2-methoxyethyl) ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropyl thioxanthone, 2-chloro-7-trifluoromethylthioxanthone, thioxanthone- 10,10-dioxide, thioxanthone-10-oxide, benzoinmethyl ether, benzoinethyl ether, isopropyl ether, benzoinisobutyl ether, benzophenon, bis(4-dimethylaminophenyl) ketone, 4,4'-bisdiethylaminobenzophenon, and a compound comprising an azido group.

13. The dental restorative material composition as claimed in claim 11, wherein the reducing agent is at least one compound selected from the group consisting of a tertiary amine, benzoyl peroxide, an organic metal compound, and a sulfinic acid derivative.

14. The dental restorative material composition as claimed in claim 13, wherein the tertiary amine is at least one compound selected from the group consisting of dimethylaminoethyl methacrylate, triethanol amine, methyl 4-dimethylaminobenzoate, ethyl 4-dimethylaminobenzoate, and isoamyl 4-dimethylaminobenzoate.

* * * * *

(12) INTER PARTES REEXAMINATION CERTIFICATE (920th)
United States Patent
Fusejima et al.

(10) Number: US 7,678,843 C1
(45) Certificate Issued: Jul. 29, 2014

(54) DENTAL RESTORATIVE MATERIAL COMPOSITION

(75) Inventors: Futoshi Fusejima, Itabashi-ku (JP); Naoko Jimbo, Itabashi-ku (JP); Shinji Kaga, Itabashi-ku (JP)

(73) Assignee: GC Corporation, Hasunuma-Cho, Itabashi-Ku, Tokyo (JP)

Reexamination Request:
No. 95/001,837, Nov. 30, 2011

Reexamination Certificate for:
Patent No.: 7,678,843
Issued: Mar. 16, 2010
Appl. No.: 11/858,403
Filed: Sep. 20, 2007

(30) Foreign Application Priority Data

Sep. 28, 2006 (JP) ................................ 2006-265998

(51) Int. Cl.
*C08J 3/28* (2006.01)
*C08F 2/50* (2006.01)
*A61K 6/04* (2006.01)
*A61K 6/083* (2006.01)
*B27K 5/00* (2006.01)

(52) U.S. Cl.
CPC . *A61K 6/043* (2013.01); *C08F 2/50* (2013.01); *B27K 5/003* (2013.01); *A61K 6/0835* (2013.01)
USPC ........... 523/117; 523/109; 523/113; 523/115; 523/116; 522/70; 522/71; 522/74; 522/81; 522/83; 522/90; 522/96; 522/150; 522/173; 522/174; 522/178; 522/181; 524/436

(58) Field of Classification Search
None
See application file for complete search history.

(56) References Cited

To view the complete listing of prior art documents cited during the proceeding for Reexamination Control Number 95/001,837, please refer to the USPTO's public Patent Application Information Retrieval (PAIR) system under the Display References tab.

*Primary Examiner* — Timothy J Kugel

(57) ABSTRACT

To provide a dental restorative material composition using an organic-inorganic composite filler having excellent surface smoothness like a natural tooth, low polymerization shrinkage, excellent X-ray contrast imaging property, similar transparency to that of a natural tooth, and no variation of transparency before and after the composition is hardened, the dental restorative material composition includes (a) a (meth) acrylate monomer, (b) an organic-inorganic composite filler having an average particle diameter of 5 to 50 μm which is made by mixing a (meth)acrylate monomer and a fine particle filler having an average primary particle diameter of 0.005 to 0.3 μm and having X-ray impermeability, (c) a fine particle filler having an average primary particle diameter of 0.005 to 0.04 μm, and (d) a photopolymerization initiator.

At the time of issuance and publication of this certificate, the patent remains subject to pending reissue application number 13/422,264 filed Mar. 16, 2012. The claim content of the patent may be subsequently revised if a reissue patent is issued from the reissue application.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-14 are cancelled.

\* \* \* \* \*